United States Patent [19]

Unger et al.

[11] Patent Number: 5,558,092
[45] Date of Patent: Sep. 24, 1996

[54] METHODS AND APPARATUS FOR PERFORMING DIAGNOSTIC AND THERAPEUTIC ULTRASOUND SIMULTANEOUSLY

[75] Inventors: Evan C. Unger; David W. Yellowhair, both of Tucson, Ariz.

[73] Assignee: ImaRx Pharmaceutical Corp., Tucson, Ariz.

[21] Appl. No.: 468,052

[22] Filed: Jun. 6, 1995

[51] Int. Cl.$^6$ .............................. A61B 8/00; A61F 7/00; A61H 1/00
[52] U.S. Cl. ............................ 128/660.03; 607/97; 601/2
[58] Field of Search ......................... 128/660.03, 662.03; 601/2; 607/97

[56] References Cited

U.S. PATENT DOCUMENTS

| | | | |
|---|---|---|---|
| 3,672,210 | 6/1972 | Cressman et al. | 73/67.9 |
| 3,735,755 | 5/1973 | Eggleton et al. | 128/24 A |
| 3,936,791 | 2/1976 | Kossoff | 340/1 R |
| 4,385,255 | 5/1983 | Yamaguchi et al. | 310/335 |
| 4,466,442 | 8/1984 | Hilmann et al. | 128/653 |
| 4,484,569 | 11/1984 | Driller et al. | 128/660 |
| 4,492,120 | 1/1985 | Lewis et al. | 73/625 |
| 4,586,512 | 5/1986 | Do-huu et al. | 128/662.03 X |
| 4,620,546 | 11/1986 | Aida et al. | 128/660 |
| 4,646,756 | 3/1987 | Watmough et al. | 128/804 |
| 4,658,828 | 4/1987 | Dory | 128/660 |
| 4,664,122 | 5/1987 | Yano | 128/660 |
| 4,757,820 | 7/1988 | Itoh | 128/660.03 |
| 4,865,042 | 9/1989 | Umemura et al. | 128/660.03 |
| 4,932,414 | 6/1990 | Coleman et al. | 128/660.09 |
| 5,005,579 | 4/1991 | Wurster et al. | 120/660.03 |
| 5,143,073 | 9/1992 | Dory | 128/660.03 |
| 5,149,319 | 9/1992 | Unger | 604/22 |
| 5,150,712 | 9/1992 | Dory | 128/660.03 |
| 5,158,071 | 10/1992 | Umemura et al. | 128/660.03 X |
| 5,182,485 | 1/1993 | de la Fonteijne | 310/334 |
| 5,209,720 | 5/1993 | Unger | 604/22 |
| 5,215,680 | 6/1993 | D'Arrigo | 252/307 |
| 5,346,000 | 5/1994 | Chapelon et al. | 128/660.03 |
| 5,380,411 | 1/1995 | Schlief | 601/2 |
| 5,391,140 | 2/1995 | Schaetzle et al. | 601/4 |
| 5,410,516 | 4/1995 | Uhlendorf et al. | 367/7 |
| 5,419,327 | 5/1995 | Rohwedder et al. | 128/660.03 |
| 5,435,311 | 7/1995 | Umemura et al. | 128/660.03 |

FOREIGN PATENT DOCUMENTS

| | | |
|---|---|---|
| 0351610 | 1/1990 | European Pat. Off. . |
| 4205030 | 9/1992 | Germany . |
| WO80/02365 | 11/1980 | WIPO . |
| WO92/17212 | 10/1992 | WIPO . |
| WO92/21382 | 12/1992 | WIPO . |
| WO94/28873 | 12/1994 | WIPO . |

OTHER PUBLICATIONS

Dickinson, R., "An Ultrasound System for Local Hyperthermia Using Scanned Focused Transducers", *IEEE Transactions on Biomedical Engineering* 1984, BME–31(1), 120–125.

Duck, F. and Starritt, "A Study of the Heating Capabilities of Diagnostic Ultrasound Beams", *Ultrasound in Med. & Biol.* 1994, 20(5), 481–492.

Fessenden, P. et al., "Experience with a Multitransducer Ultrasound System for Localized Hyperthermia of Deep Tissues", *IEEE Transactions on Biomedical Engineering* 1994, BME–31(1), 126–135.

(List continued on next page.)

*Primary Examiner*—Francis Jaworski
*Attorney, Agent, or Firm*—Woodcock Washburn Kurtz Mackiewicz & Norris

[57] ABSTRACT

Methods and apparatus for performing diagnostic ultrasound simultaneously with the application of therapeutic ultrasonic waves are disclosed. The methods and apparatus are particularly advantageous in performing ultrasonic imaging of a region of a patient while simultaneously applying therapeutic ultrasonic waves to the region for the purpose of rupturing vesicles administered to that region for purposes such as enhanced cavitation or the targeted release of a bioactive agent into the region. An operator is able to monitor the rupture of vesicles in real time.

27 Claims, 7 Drawing Sheets

OTHER PUBLICATIONS

Frederiksen, F., "Guidelines for Characterization of Ultrasound Transducers", *Ultrasonics* 1992, 30(2), 119–121.

Gautherie, M., ed., "Ultrasound Hyperthermia: Summary Proceedings of COMAC–BME Workshop", with contributing authors Hynynen, ter Haar and Watmough, *Ultrasonics* 1992, 30(2), 113–118.

Hahn, G., "Hyperthermia for the Engineer: A Short Biological Primer", *IEEE Transactions on Biomedical Engineering* 1984, BME–31(1), 3–8.

Hand, J. W., "III. Control of Ultrasound Hyperthermia Treatment. Thermometry in Ultrasonic Fields", *Ultrasonics* 1992, 30(2), 125–128.

Hekkenberg, R. T. et al., "Development of Standard Measurement Methods for Essential Properties of Ultrasound Therapy Equipment", *Ultrasound in Med. & Biol.* 1994, 20(1), 83–98.

Hinders, M. K. et al., "An Analytic Solution for Energy Deposition in Model Spherical Tumours Undergoing Ultrasound–hperthermia Treatments", *Phys. Med. Biol.* 1994, 39, 107–132.

Hynynen, K., "Acoustic Power Calibrations of Cylindrical Intracavitary Ultrasound Hyperthermia Applicators", *Med. Phys.* 1993, 20(1), 129–134.

Kazys, R. and Svilainis, "Analysis of Adaptive Imaging Algorithms for Ultrasonic Non–destructive Testing", *Ultrasonics* 1995, 33(1), 19–30.

Lagendijk, J., "IV. Thermal Modelling and Treatment Planning. Thermal Modelling and Treatment Planning for Scanned Focused Ultrasound", *Ultrasonics* 1992, 30(2), 134–135.

Özyar, M. and Köymen, "Non–invasive Method for in situ Estimation of Intensity Using Non–linear Effects in Ultrasound Hyperthermia", *Ultrasonics* 1992, 30(2), 123–124.

Frey, P. et al., "Three–dimensional Characterization of Ultrasonic Fields for Hyperthermia Treaments", *Ultrasonics* 1992, 30(2), 121–123.

Lovejoy, A. et al., "A Novel 8–bit Ultrasound Phased–array Controller for Hyperthermia Applications", *Ultrasonics* 1995, 33(1), 69–73.

Lu, J.–Y. et al., "Biomedical Ultrasound Beam Forming", *Ultrasound in Med. & Biol.* 1994, 20(5), 403–428.

Miller, D. L., "Ultrasonic Detection of Resonant Cavitation Bubbles in a Flow Tube by their Second–harmonic Emissions", *Ultrasonics* 1981, 217–224.

Roy, R. et al., "An Acoustic Backscattering Technique for the Detection of Transient Cavitation Produced by Microsecond Pulses of Ultrasound", *J. Acoust. Soc. Am.* 1990, 87(6), 2451–2458.

Saitoh, S. et al., "A Dual Frequency Ultrasonic Probe for Medical Applications", *IEEE Transactions on Ultrasonics, Ferroelectrics, and Frequency Control* 1995, 42(2), 294–300.

Savakus, H. P. et al., "PZT–Epoxy Piezoelectric Transducers: A Simplified Fabrication Procedure", *Mat. Res. Bull.* 1981, 16, 677–680.

Song, C. et al., "Implication of Blood Flow in Hyperthermic Treatment of Tumors", *IEEE Transactions on Biomed. Engineering* 1984, BME–31(1), 9–15.

Vernon, C. C. et al., "Scanned Focused Ultrasound Hyperthermia Using the Sonotherm 6500 System", *Ultrasonics* 1992, 30(2), 141–143.

Wu, J. et al., "Effect of Acoustic Streaming on Ultrasonic Heating", *Ultrasound in Med. & Biol.* 1994, 20(2), 195–201.

Gautherie, M. and Frey, "Toward Clinical Treatment Planning for Ultrasound Hyperthermia", *Ultrasonics* 1992, 30(2), 135–137.

Nguyen, M. T. and Faust, "Possibilities and Limitations of Temperature Monitoring Using Ultrasound Techniques", *Ultrasonics* 1992, 30(2), 128–131.

Nadi, M. et al., "Ultrasound Thermography: Theoretical Aspects and Feasibility", *Ultrasonics* 1992, 30(2), 131–133.

Acoustic Imaging; AI5200; Convex Curved Linear Array Ultrasound Transducers Operator's Manual, Nov. 20, 1989, 4700–0003–1C, p. 4.

METHODS AND APPARATUS FOR PERFORMING DIAGNOSTIC AND THERAPEUTIC ULTRASOUND SIMULTANEOUSLY

BACKGROUND OF THE INVENTION

1. Field of the Invention

The present invention relates to the fields of diagnostic and therapeutic ultrasound, and more particularly, to novel methods and apparatus for performing diagnostic ultrasound simultaneously with the application of therapeutic ultrasonic waves to a region of a patient.

2. Background of the Invention

Diagnostic ultrasound refers to the imaging of a region of a human or animal patient using an ultrasound transducer to generate and receive ultrasonic waves. Typically, the transducer is placed on the patient's body over a region to be imaged and ultrasonic waves generated by the transducer are then directed at the region. The transducer then receives reflected ultrasonic waves from the region and converts the received waves into electrical signals from which an image is generated. Generally, better images are obtained with diagnostic ultrasound when higher frequency, lower energy ultrasonic waves are employed. Contrast agents can also be used to improve the quality of images obtained via diagnostic ultrasound. Exemplary contrast agents include, for example, suspensions of solid particles, emulsified liquid droplets, and gas-filled bubbles. See, e.g., Hilmann et al., U.S. Pat. No. 4,466,442, and published International Patent Applications WO 92/17212 and WO 92/21382.

Ultrasound has also been used in various therapeutic applications. One therapeutic use of ultrasound is known as hyperthermia. Hyperthermia involves insonating a targeted tissue mass, such as a tumor, with focused ultrasonic waves in order to heat the targeted mass. Application of heat to the tissue mass results in a retardation of growth of, or a shrinking of, the mass. The heating effects of therapeutic ultrasound can be enhanced by the introduction of microbubbles into the region under treatment, as described in D'Arrigo, U.S. Pat. No. 5,215,680.

Another therapeutic use of ultrasound, which is described in published International Patent Application WO 94/28873, involves administering a quantity of vesicles to a patient and monitoring the vesicles, for example using diagnostic ultrasound, until the presence of the vesicles is detected in a region of interest. Therapeutic ultrasonic waves are then applied to the region in order to rupture the vesicles for therapeutic purposes. For example, the vesicles may be combined with a bioactive agent that is released upon rupture of the vesicles, thus achieving targeted delivery of the bioactive agent in the region of interest.

Therapeutic ultrasound is typically carried out at different frequencies than diagnostic ultrasound. Specifically, it is desirable to perform therapeutic ultrasound at lower frequencies in order to achieve low attenuation, whereas higher frequencies are employed in diagnostic ultrasound to obtain better resolution.

There has been some effort in the prior art to provide systems that permit diagnostic ultrasound to be carried out simultaneously with therapeutic ultrasound, particularly therapeutic applications involving hyperthermia. Schaetzle, et al., U.S. Pat. No. 5,391,140, describe an apparatus having a diagnostic ultrasound capability that operates simultaneously with the application of therapeutic acoustic waves for localized hyperthermia. The system employs a transducer assembly that includes both diagnostic transducer elements and therapeutic transducer elements. The diagnostic transducer elements form a central array that is surrounded by the therapeutic transducer elements. Placing the therapeutic transducer elements outwardly of the centrally located diagnostic transducer elements enables the therapeutic acoustic waves to be more accurately focused in hyperthermia applications to achieve greater heating of biological tissues. However, the central location of the diagnostic transducer elements limits image quality and resolution.

Driller et al., U.S. Pat. No. 4,484,569, Coleman et al., U.S. Pat. No. 4,932,414 and Wurster et al., U.S. Pat. No. 5,005,579 all describe various systems that combine diagnostic ultrasound capabilities with therapeutic, hyperthermia capabilities, although not necessarily simultaneously.

The transducer assemblies and systems employed in these prior art systems are relatively complex and expensive to manufacture. Moreover, to the extent that these systems may be capable of performing diagnostic and therapeutic ultrasound simultaneously, their therapeutic ultrasound capabilities are designed primarily for, and therefore limited to, use in hyperthermia applications. None of these systems are suitable for carrying out ultrasonic imaging simultaneously with the ultrasonic rupture of vesicles for purposes such as enhanced cavitation or the targeted delivery of a bioactive agent to a region of a patient. Accordingly, methods and apparatus for providing such a capability are needed. The present invention satisfies this need.

SUMMARY OF THE INVENTION

The present invention is directed to novel methods and apparatus for performing diagnostic ultrasound simultaneously with the application of therapeutic ultrasonic waves to a region of a patient. In particular, the methods and apparatus of the present invention are advantageous in performing ultrasonic imaging of a region of a patient while simultaneously applying therapeutic ultrasonic waves to the region in order to rupture vesicles administered to that region for various purposes, such as, for example, the targeted release of a bioactive agent combined with the vesicles. The methods and apparatus of the present invention allow an operator to monitor the rupture of vesicles in real time.

According to one aspect of the present invention, an ultrasonic transducer assembly comprises a plurality of therapeutic transducer elements for generating therapeutic ultrasonic waves, and a plurality of diagnostic transducer elements for generating and/or receiving diagnostic ultrasonic waves. The therapeutic and diagnostic transducer elements are arranged on a common platform having a substantially planar upper surface. The plurality of therapeutic transducer elements are disposed on the planar surface of the platform centrally of the plurality of diagnostic transducer elements. Placement of the plurality of diagnostic transducer elements outwardly from the centrally located plurality of therapeutic transducer elements enlarges the field of view of the ultrasonic transducer assembly, increases the imaging sensitivity of the assembly and increases the resolution of images obtained using the ultrasonic transducer assembly.

The ultrasonic transducer assembly of the present invention is capable of performing diagnostic ultrasound in a region of a patient simultaneously with the application of therapeutic ultrasonic waves to that region. The ultrasonic transducer assembly of the present invention can be used in a wide variety of therapeutic applications, including hyperthermia, cavitation and the like. The ultrasonic transducer assembly of the present invention is particularly advantageous for carrying out ultrasonic imaging of vesicles administered to a region of a patient simultaneously with the application of therapeutic ultrasonic waves in order to rupture the vesicles for purposes, such as, for example, the targeted release of a bioactive agent combined with the vesicles.

Another aspect of the present invention relates to a method of carrying out ultrasonic imaging simultaneously with the ultrasonic rupture of vesicles in a region of a patient for purposes, such as, for example, enhanced cavitation or the targeted delivery of a bioactive agent combined with the vesicles. The method comprises the steps of (i) administering to the patient a quantity of vesicles; (ii) insonating the vesicles in a region of the patient with therapeutic ultrasonic waves at a frequency and energy to cause the vesicles to rupture; and (iii) simultaneously receiving ultrasonic emissions from the insonated vesicles at a harmonic of the frequency of the therapeutic ultrasonic waves and generating an image of said region from the received ultrasonic emissions. Simultaneous imaging allows an operator to monitor the rupture of the vesicles in real time.

These and other features and advantages of the present invention will become evident hereinafter.

BRIEF DESCRIPTION OF THE DRAWINGS

The foregoing summary, as well as the following detailed description of the invention, is better understood when read in conjunction with the appended drawings. For the purpose of illustrating the invention, there is shown in the drawings embodiments that are presently preferred, it being understood, however, that the invention is not limited to the specific methods and instrumentalities disclosed. In the drawings:

FIGS. 10 (a) and (b) show a transesophageal probe incorporating an ultrasonic transducer assembly in accordance with the present invention;

FIGS. 11 (a) and (b) show an intracavitary probe incorporating an ultrasonic transducer assembly in accordance with the present invention;

FIGS. 12 (a) and (b) show a second configuration of an intracavitary probe incorporating an ultrasonic transducer assembly in accordance with the present invention.

DETAILED DESCRIPTION OF THE INVENTION

The present invention is directed to novel methods and apparatus for performing diagnostic ultrasound simultaneously with the application of therapeutic ultrasonic waves to a region of a patient. In particular, the methods and apparatus of the present invention are advantageous in performing ultrasonic imaging of a region of a patient while simultaneously applying therapeutic ultrasonic waves to the region for the purpose of rupturing vesicles administered to that region for various purposes, such as, for example, the targeted release of a bioactive agent into the region. The methods and apparatus of the present invention allow an operator to monitor the rupture of vesicles in real time.

As employed above and throughout the disclosure, the following terms, unless otherwise indicated, shall be understood to have the following meanings.

"Lipid" refers to a synthetic or naturally-occurring amphipathic compound which comprises a hydrophilic component and a hydrophobic component. Lipids include, for example, fatty acids, neutral fats, phosphatides, glycolipids, aliphatic alcohols and waxes, terpenes and steroids.

"Lipid composition" refers to a composition which comprises a lipid compound. Exemplary lipid compositions include suspensions, emulsions and vesicular compositions.

"Lipid formulation" refers to a composition which comprises a lipid compound and a bioactive agent.

"Vesicle" refers to a spherical entity which is characterized by the presence of an internal void. Preferred vesicles are formulated from lipids, including the various lipids described herein. In any given vesicle, the lipids may be in the form of a monolayer or bilayer, and the mono- or bilayer lipids may be used to form one or more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

"Vesicular composition" refers to a composition which is formulated from lipids and which comprises vesicles.

"Vesicle formulation" refers to a composition which comprises vesicles and a bioactive agent.

"Liposome" refers to a generally spherical cluster or aggregate of amphipathic compounds, including lipid compounds, typically in the form of one or more concentric layers, for example, bilayers. They may also be referred to herein as lipid vesicles.

"Patient" refers to animals, including mammals, preferably humans.

"Bioactive agent" refers to a substance which is used in connection with an application that is therapeutic or diagnostic in nature, such as in methods for diagnosing the presence or absence of a disease in a patient and/or in methods for the treatment of disease in a patient. As used herein, "bioactive agent" refers also to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids and genetic material, including nucleosides, nucleotides and polynucleotides.

"Diagnostic agent" refers to any agent which is used in connection with methods for diagnosing the presence or absence of a disease in a patient. Exemplary diagnostic agents include, for example, contrast agents for use in connection with ultrasound, magnetic resonance imaging or computed tomography of a patient, "Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

"Pharmaceutical" or "drug" refers to any therapeutic or prophylactic agent which is used in the treatment (including the prevention, diagnosis, alleviation, or cure) of a malady, affliction, disease or injury in a patient. Therapeutically useful peptides, polypeptides and polynucleotides are included within the meaning of the term pharmaceutical or drug.

"Stabilizing material" refers to a substance which is biocompatible and which is capable of promoting the formation of vesicles in a lipid composition. As used herein, "stabilizing material" refers also to a substance which is biocompatible and which is capable of improving the stability of a vesicle. The stabilizing material may comprise a polymer. "Polymer", as used herein, refers to molecules formed from the chemical union of two or more repeating units. Accordingly, included within the term "polymer" are, for example, dimers, trimers and oligomers. The stabilizing material may also comprise a non-polymeric material, including, for example, monomeric molecules. Encompassed also in the definition of "stabilizing material" are certain of the present bioactive agents. The stabilizing material may be neutral or positively or negatively charged. Preferred among the neutral stabilizing materials are polar materials.

"Vesicle stability" refers to the ability of gas-filled vesicles to retain the gas entrapped therein after being exposed, for about one minute, to a pressure of about 300 mm Hg. Vesicle stability is measured in percent (%), this being the fraction of the amount of gas which is originally entrapped in the vesicle and which is retained after release of the pressure. Vesicle stability includes reference also to "vesicle resilience" which refers to the ability of a vesicle to return to its original size after release of the pressure.

"Viscosity" refers to the internal friction of a fluid that is measurable using standard viscosity-measuring means, such as a viscometer.

"Raising viscosity" refers to the increase of viscosity by greater than about 20%.

"Non-covalent association" refers to intermolecular interaction among two or more separate molecules, which interaction does not involve a covalent bond. Intermolecular interaction is dependent upon a variety of factors, including, for example, the polarity of the involved molecules, the charge (positive or negative), if any, of the involved molecules, and the like. Non-covalent associations are preferably selected from the group consisting of ionic interaction, dipole-dipole interaction and van der Waal's forces and combinations thereof.

"Ionic interaction" refers to intermolecular interaction among two or more molecules, each of which is positively or negatively charged. Thus, for example, "ionic interaction" refers to the attraction between a first, positively charged molecule and a second, negatively charged molecule. Exemplary ionic interactions include, for example, the attraction between a negatively charged stabilizing material, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole-dipole interaction" refers to the attraction of the positive end of a first polar molecule to the negative end of a second polar molecule. Dipole-dipole interactions are exemplified, for example, by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" refers also to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

Terms such as "comprising a bioactive agent", "in combination with a bioactive agent," "combined with a bioactive agent" and the like, refer to the incorporation of a bioactive agent with a lipid composition. The bioactive agent can be combined with the lipid composition in any of a variety of ways. For example, when the lipid composition is in the form of a vesicular composition, the bioactive agent may be entrapped within the internal void of the vesicle. The bioactive agent may also be integrated within the layer(s) or wall(s) of the vesicle, for example, by being interspersed among lipids which are contained within the vesicular layer(s) or wall(s). In addition, it is contemplated that the bioactive agent may be located on the surface of a vesicle. In this case, the bioactive agent may interact chemically with the surface of the vesicle and remain substantially adhered thereto. Such interaction may take the form of, for example, non-covalent association. The interaction may result in the stabilization of the vesicle.

"Coat" or "coating" refers to the interaction of the stabilizing material with the lipid and/or vesicles and includes non-covalent interaction.

"Insonate" and variations thereof means to expose to ultrasonic waves.

Additional details concerning vesicles, vesicle compositions and vesicle formulations, including methods of producing the same, are provided in co-pending, commonly assigned, U.S. patent application Ser. No. 08/417,238, filed Apr. 5, 1995, entitled "NOVEL COMPOSITIONS OF LIPIDS AND STABILIZING MATERIALS", and in co-pending, commonly assigned, U.S. patent application Ser. No. 08/076,250, filed Jun. 11, 1993, entitled "NOVEL THERAPEUTIC DRUG DELIVERY SYSTEMS", as well as their respective progeny, the disclosures of all of which are incorporated herein by reference in their entireties.

One aspect of the present invention is directed to an ultrasonic transducer assembly for performing diagnostic ultrasound in a region simultaneously with the application of therapeutic ultrasonic waves to the region. The ultrasonic transducer assembly of the present invention comprises a plurality of therapeutic transducer elements for generating therapeutic ultrasonic waves, and a plurality of diagnostic transducer elements for generating and/or receiving diagnostic ultrasonic waves. The therapeutic and diagnostic transducer elements are arranged on a common platform having a substantially planar upper surface. The plurality of therapeutic transducer elements are disposed on the planar surface of the platform centrally of the plurality of diagnostic transducer elements. Placement of the plurality of diagnostic transducer elements outwardly from the centrally located plurality of therapeutic transducer elements enlarges the field of view of the ultrasonic transducer assembly, increases the imaging sensitivity of the assembly and increases the resolution of images obtained using the ultrasonic transducer assembly.

The ultrasonic transducer assembly of the present invention is capable of applying and receiving diagnostic ultrasonic waves to and from a region of a patient, simultaneously with the application of therapeutic ultrasonic waves to that region. The ultrasonic transducer assembly of the present invention can be used in a wide variety of therapeutic applications, including hyperthermia, cavitation and the like. The ultrasonic transducer assembly of the present invention is particularly advantageous for carrying out ultrasonic imaging simultaneously with the ultrasonic rupture of vesicles for various purposes, such as, for example, enhanced cavitation or the targeted release of bioactive agents combined with the vesicles. With the ultrasonic transducer assembly of the present invention, an operator can monitor the rupture of vesicles in real time.

Figure 1:
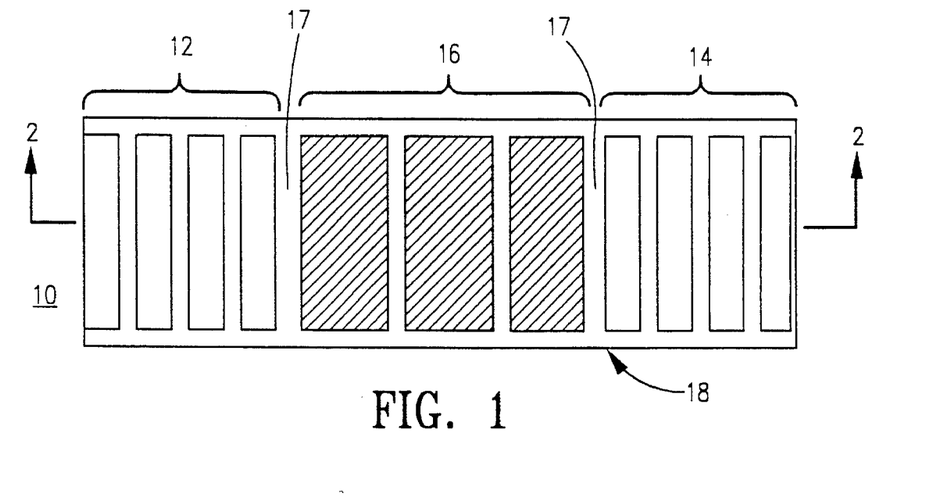
FIG. 1 is top view of a portion of an ultrasonic transducer assembly in accordance with one embodiment of the present invention.

Referring to the drawings wherein like numerals indicate like elements throughout, there is shown in FIG. 1 a top view of a first embodiment of an ultrasonic transducer assembly 10 according to the present invention. In accordance with this first embodiment, the plurality of therapeutic transducer elements comprises a linear array 16 of therapeutic transducer elements. As used herein, the term "therapeutic transducer element" means a transducer element having acoustic properties suitable for generating ultrasonic waves at a frequency and energy useful in the practice of therapeutic ultrasound, and preferably having acoustic properties suitable for generating ultrasonic waves of a frequency and energy sufficient to rupture vesicles in vivo and/or in vitro. Preferably, the therapeutic transducer elements of the linear array 16 are capable of generating ultrasonic waves at a frequency in the range of about 0.25 to about 100 megahertz (MHz), more preferably in the range of about 0.75 MHz to about 3.0 MHz, most preferably in the range of about 1.0 MHz to about 2.0 MHz. The frequency at which a transducer element generates ultrasonic waves is, in part, a function of the thickness of the transducer element.

Further according to the first embodiment of the ultrasonic transducer assembly of the present invention, the second plurality of transducer elements comprises first and second linear arrays of diagnostic transducer elements 12 and 14, respectively, disposed on opposite sides of the linear array of therapeutic transducer elements 16. As used herein, the term "diagnostic transducer element" means a transducer element having acoustic properties suitable for generating and receiving acoustic signals in diagnostic ultrasound (imaging) applications, including those based on harmonic imaging techniques. Preferably, the diagnostic transducer elements of the first and second arrays 12, 14 are capable of generating and receiving ultrasonic waves at a frequency in the range of about 1.0 MHz to about 10.0 MHz.

Figure 2:
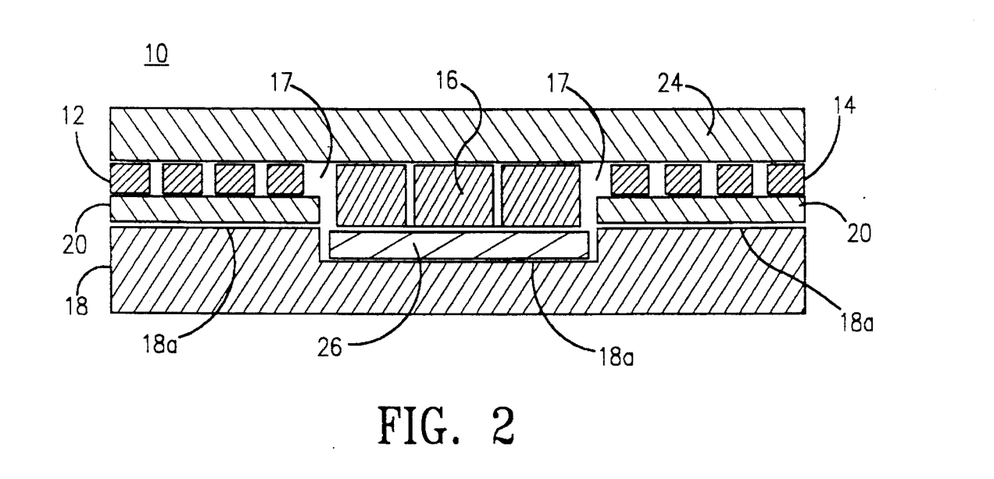
FIG. 2 is a cross-sectional view of the ultrasonic transducer assembly of FIG. 1 taken along line 2—2 of FIG. 1.

FIG. 2 is a cross-sectional view of the transducer assembly 10 of FIG. 1, illustrating further details of the assembly 10 in accordance with the present embodiment. As shown, the respective linear arrays of transducer elements 12, 14, 16 are arranged on a common platform 18 having a substantially planar upper surface 18a. In the present embodiment, a central portion of the upper surface 18a of the platform is stepped to accommodate the greater thickness of the linear array of therapeutic transducer elements 16. A first backing material 26 is disposed between the linear array of therapeutic transducer elements 16 and the upper surface 18a of the platform 18. A second backing material 20 is disposed between each of the linear arrays of diagnostic transducer elements 12, 14 and the upper surface 18a of the platform. A common layer of an impedance matching material is provided on the opposite surfaces of each linear array of transducer elements 12, 14, 16, as shown.

The linear array of therapeutic transducer elements 16 can be operated in a continuous wave mode, or it can be operated in a pulse repetition frequency (PRF) mode selectable by an operator. The amount of energy supplied to the therapeutic transducer elements can be controlled by the operator, as can the depth of treatment. When employed as described below to rupture vesicles for therapeutic purposes, the linear array of therapeutic transducer elements 16 is preferably operated at energies in the range of 0.05 to 5.0 W/cm$^2$, and more preferably in the range of about 0.2 to about 2.5 W/cm$^2$.

The first and second linear arrays of diagnostic transducer elements can be used to perform imaging tasks in a conventional manner and can be operated in several different modes. In one mode, each of the arrays 12, 14 is operated independently to create respective images on separate display screens simultaneously. In this mode, each linear array 12, 14 would transmit and receive its own ultrasonic waves. In another operating mode, one of the linear arrays 12, 14 can act as the transmitting array, and the other can act as the receiving array. The resultant image would be in the vicinity of the focal point of the array of therapeutic transducer elements 16. This modality would require conventional beam steering for proper focusing.

In a preferred imaging modality, described more fully below in connection with a novel method of the present invention, the linear array of therapeutic transducer elements 16 generates therapeutic ultrasonic waves having a frequency and energy sufficient to rupture a quantity of vesicles administered to a patient, and the two outer arrays of diagnostic transducer elements 12, 14 are used to receive harmonic emissions from the insonated vesicles so that the vesicles can be imaged in real time as they rupture. Preferably, the first and second arrays are used to receive second harmonic emissions from the insonated vesicles, i.e., emissions at twice the frequency of the incident, therapeutic ultrasonic waves. However, receipt of emissions at other harmonics of the incident waves, including both even and odd harmonics, can also be performed.

Both the therapeutic and diagnostic transducer elements are preferably formed of a ceramic piezoelectric material, such as, for example, lead zirconate titanate (PZT). Other piezoelectric materials can, however, be employed. As those skilled in the art know, the thickness and center-to-center spacing of adjacent transducer elements in a linear array determines the center, or resonant, frequency of the array. To achieve a desired center frequency, the thickness and center-to-center spacing of adjacent elements should be one-half the wavelength of an ultrasonic wave at that frequency. For example, for a desired center frequency of 3.5 MHz, the thickness and center-to-center spacing of adjacent transducer elements would be approximately $2.3 \times 10^{-2}$ cm. The individual transducer elements of each array 12, 14, 16 can be formed in any conventional manner. For example, the transducer elements can be cut from a sheet of piezoelectric material using a diamond-bit saw, or alternatively, can be etched using a buffered solution of hydrofluoric acid (HF).

The first backing material 26 disposed between the linear array of therapeutic transducer elements 16 and the platform 18 preferably has an acoustic impedance suitable for the transmission of therapeutic ultrasonic waves. In the present embodiment, the first backing material preferably has an acoustic impedance in the range of about $2 \times 10^6$ Kg/m²/s to about $3 \times 10^6$ Kg/m²/s, which is suitable for transmission of therapeutic waves having frequencies and energies in the ranges set forth above. The first backing material may comprise any one of a variety of suitable materials. Preferably, the first backing material comprises a polymer matrix material that is bonded solidly to the linear array 16 of therapeutic transducer elements. For example, epoxy with tungsten powder can be used. Alternatively, the first backing material 26 can comprise air.

The second backing material 20 disposed between each of the linear arrays of diagnostic transducer elements 12, 14 and the platform 18 preferably has an acoustic impedance suitable for the transmission and reception of diagnostic ultrasonic waves, preferably diagnostic ultrasonic waves having a frequency in the range of about 1.0 to about 10.0 MHz. Preferably, the second backing material has an acoustic impedance of about $7 \times 10^6$ Kg/m²/s. The second backing material may comprise any one of a variety of suitable materials. Preferably, the second backing material comprises a polymer matrix material that is bonded solidly to the respective linear arrays 12, 14 of diagnostic transducer elements. For example, epoxy with tungsten powder may be used. Generally, the acoustic impedance of the first backing material 26 is lower than that of the second backing material 20.

The layer of matching material 24 preferably has an acoustic impedance that couples the mismatch of the acoustic impedance of the transducer elements to that of the biological tissue of the patient. Preferably, the matching material 24 has an acoustic impedance between that of the transducer elements and biological tissue. Any of a variety of suitable materials can be employed to form the matching layer 24, such as, for example, acrylic with epoxy.

Preferably, the therapeutic transducer elements 16 are isolated from the diagnostic transducer elements 12, 14 using a material that has a heavily damped acoustic impedance. Preferably, such a material would be located at areas 17 of the transducer assembly 10 of FIGS. 1 and 2. An isolating material will reduce the acoustic interference from the therapeutic transducer elements 16, which can add noise to the ultrasonic echos received by the diagnostic transducer elements 12, 14 during simultaneous imaging. A variety of heavily damped materials can be employed as the isolating material, such as, for example, neoprene or air.

Figure 3:
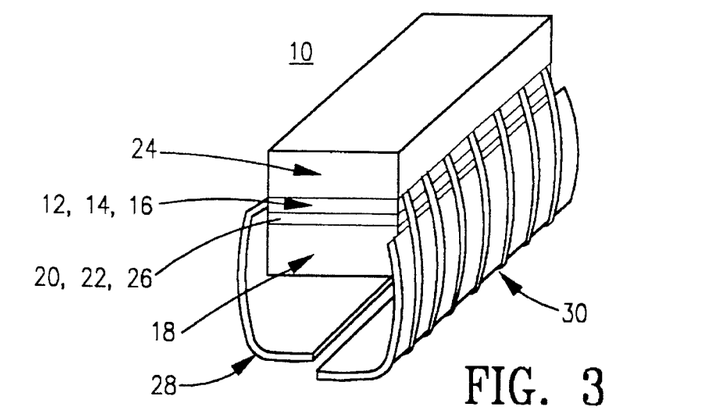
FIG. 3 is a perspective view of the ultrasonic transducer assembly of FIG. 2.

FIG. 3 is a perspective view of the transducer assembly of FIG. 2 illustrating the attachment of electrodes to the transducer elements of the respective linear arrays 12, 14, 16. Electrodes (not shown) on the top and bottom of each transducer element are connected to respective flexible circuit boards 28 and 30. The flexible circuit board 28 will connect one electrode on each transducer element to ground, and the other flexible circuit board 30 will connect the other electrode on each transducer element to an anode. Wire bonding or TAB bonding can be used to make the appropriate connections.

Figure 4:
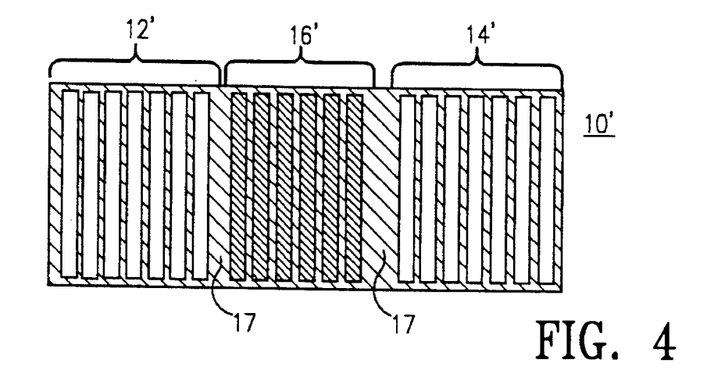
FIG. 4 illustrates a second embodiment of an ultrasonic transducer assembly in accordance with the present invention.

The number of elements in each linear array 12, 14, 16 is not limited to the number of elements illustrated in FIGS. 1 and 2. FIG. 4 shows a second embodiment of an ultrasonic transducer assembly 10' in accordance with the present invention. In this second embodiment, the ultrasonic transducer assembly has an increased number of elements in each linear array 12', 14', 16'. Increasing the number of transducer elements in each linear array 12, 14, 16 has the advantages of increased imaging resolution and higher therapeutic output.

Apodization techniques can be used with each linear array 12, 14, 16. Apodization will enhance contrast resolution and will eliminate side lobe artifacts in the linear arrays of diagnostic transducer elements 12, 14. Apodization will also minimize side lobe artifacts in the linear array of therapeutic transducer elements 16. Conventional beam steering techniques can be employed to focus the ultrasonic output of the linear array of therapeutic transducer elements 16, as well as to focus the linear arrays of diagnostic transducer elements 12, 14 in both transmit and receive modes. The maximum angle for beam steering should be kept below 25 degrees to help minimize grating lobes and side lobes that can affect image resolution.

Figure 5:
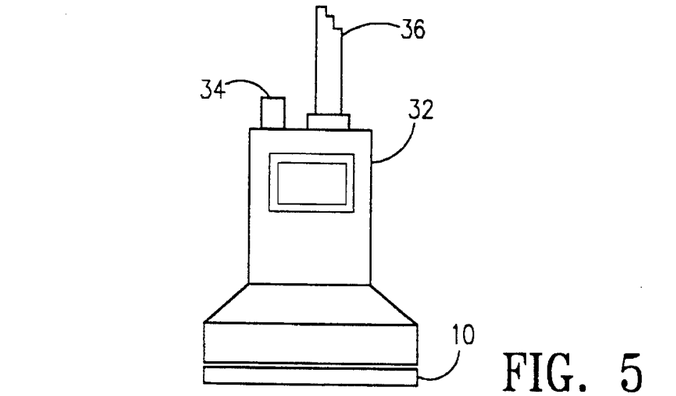
FIG. 5 shows a hand-held unit incorporating an ultrasonic transducer assembly of the present invention.

FIG. 5 shows a hand-held unit incorporating the ultrasonic transducer assembly 10 of the present invention. A housing 32 carries the transducer assembly 10 at one end. A cable 36 connects the unit to an ultrasound system, described hereinafter in greater detail. A button 34 provides selective activation of the linear array of therapeutic transducer elements 16. The two arrays of diagnostic transducer elements 12, 14 can be used to locate a region to be treated. Once the desired region is located, the linear array of therapeutic transducer elements 16 can be activated by depressing the button 34.

The ultrasonic transducer assembly of the present invention, and the hand-held unit illustrated in FIG. 5, are preferably constructed of non-magnetic materials that are compatible with magnetic resonance imaging (MRI) modalities. The contacts of the flexible circuits 28, 30 are preferably made of copper, or similar materials. Housings are preferably made of non-magnetic materials such as stainless steel or a polymer material.

Figure 6:
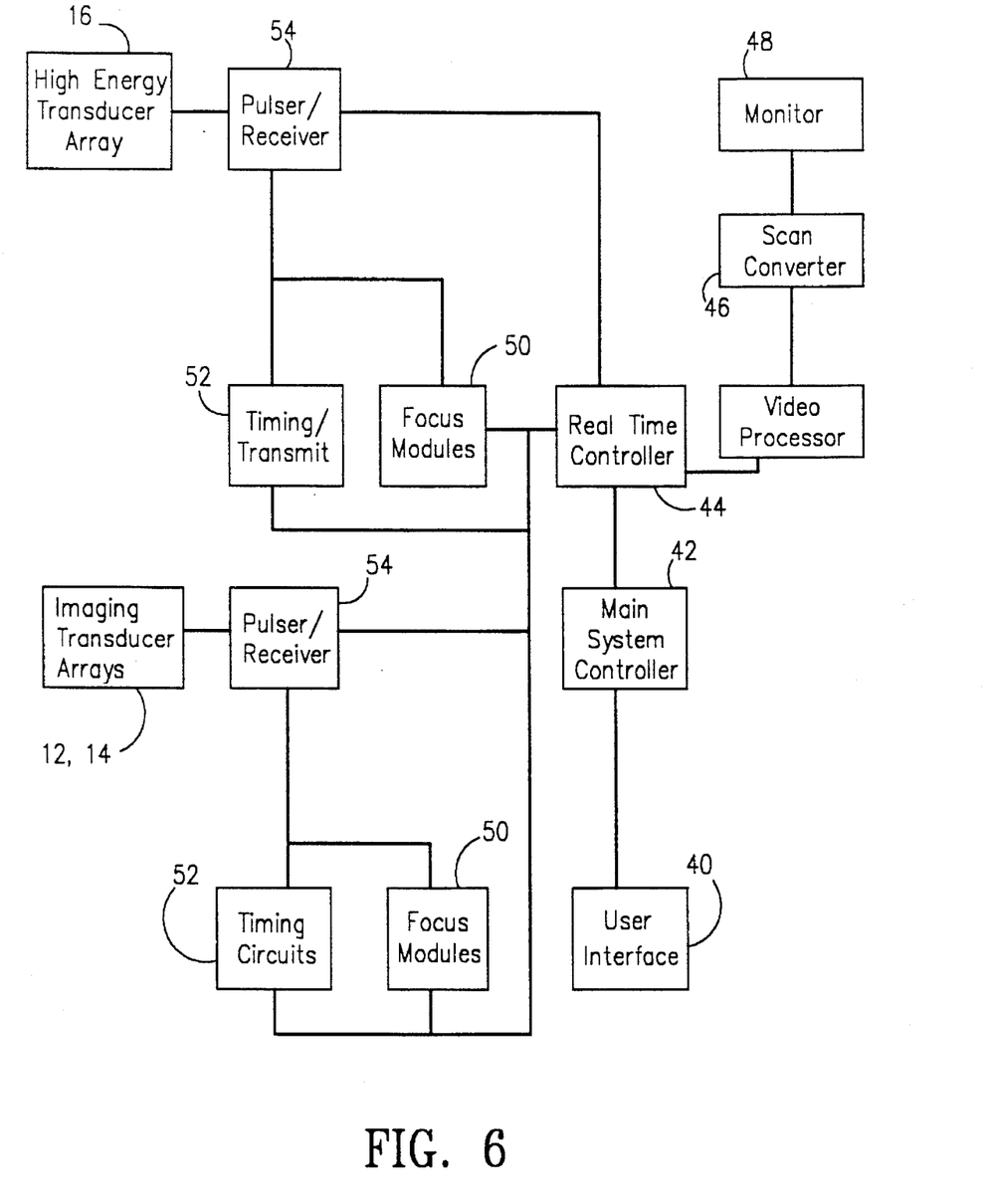
FIG. 6 is a block diagram of apparatus for performing simultaneous diagnostic and therapeutic ultrasound using the ultrasonic transducer assembly of the present invention.

FIG. 6 is a block diagram of an ultrasound system for use with the ultrasonic transducer assembly 10 of the present invention. A user interface 40 allows an operator to control various parameters, in a conventional manner, during both diagnostic and therapeutic operation of the transducer assembly 10. For example, the user can adjust the output energy of the transducer elements and can adjust the depth of focus of the emitted energy. A main system controller 42 controls the overall functioning of the ultrasound system, and can be implemented using a standard IBM PC/XT compatible board.

The main system controller 42 commands a real time controller 44 to establish pulse train and timing parameters to achieve the desired diagnostic and therapeutic functions input by the operator. The real time controller 44 controls conventional focus modules 50, transmit/timing modules 52 and pulse/receiver modules 54 separately for the arrays of diagnostic and therapeutic transducer elements, e.g., linear arrays 12, 14 and 16. The focus modules 50, transmit/timing modules 52 and pulser/receiver modules 54 handle selection of the acoustic line of sight and focusing for both the diagnostic transducer arrays 12, 14 and the therapeutic transducer array 16. The transmit/timing modules 52 control the pulser/receiver modules 54 and enable the proper channels to form appropriate apertures for both the diagnostic and therapeutic transducer arrays 12, 14, 16. The pulser/receiver modules 54 generate the appropriate pulse trains for the individual transducer elements under control of the transmit/timing modules 52. Pulse width, duration, power, aperture size, and other parameter are controlled by the real time controller 44 in accordance with parameters input by the operator. For best imaging resolution, the ratio of focal distance to aperture size should be kept relatively low.

A high resolution monitor 48 provides the video display for the system. A video processor 45 serves as a selector and signal processor for acoustic echo information received by the diagnostic transducer arrays 12, 14. The video processor creates a single, analog stream of filtered, logarithmically compressed acoustic echo signals. Pre- and post-signal detection techniques, such as time gain compensation, are employed to compensate for attenuation versus penetration depth. A scan converter 46 converts the output of the video processor 45 into a signal compatible with the monitor 48 to provide real-time display of two-dimensional ultrasound images.

Figure 7:
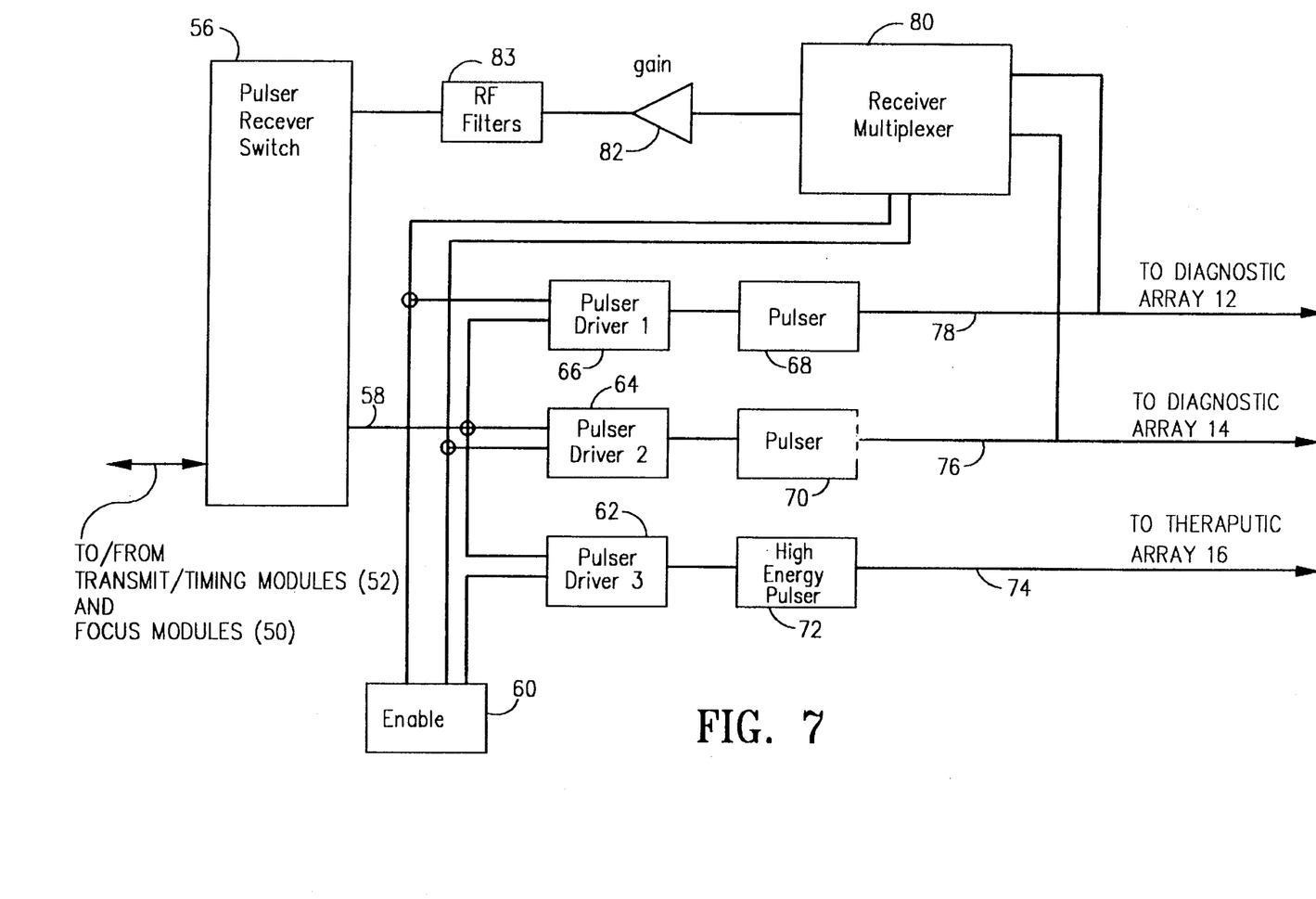
FIG. 7 is a block diagram illustrating further details of the circuitry of FIG. 6.

FIG. 7 is a block diagram illustrating further details of the pulser/receiver modules 54 of FIG. 6. A pulser/receiver switch 56, which interfaces with the transmit/timing modules 52 and focus modules 50, controls the transmit and receive operations of the respective arrays of transducer elements 12, 14, 16. For a transmit operation, the pulser/receiver switch 56 sends signals to the appropriate pulser drivers 62, 64, 66. The pulser drivers 62, 64, 66 can be individually enabled via block 60. Each transducer element of each array 12, 14, 16 is driven separately via respective element buses 74, 76, 78. The actual electrical signals are provided to the respective transducer elements by pulser circuits 68, 70 and 72. A receiver multiplexer 80 controls the diagnostic transducer arrays 12, 14 in receive mode in order to "listen" for returned echos. When the diagnostic transducers 12, 14 are used in a transmit mode, the receiver multiplexer creates an open circuit to the receiver gain circuitry 82 so that the gain circuitry 82 does not get damaged.

RF filters 83 are employed to select a desired frequency range for receiving returned echos via the diagnostic transducer elements 12, 14. An RF filter allows signals in a specified frequency range to pass while rejecting all other frequencies as noise. Because biological tissues act as a low-pass filter to incident ultrasonic waves, when constructing an RF filter for maximum penetration, the RF filter should be designed with a center frequency that is below the center frequency of the diagnostic transducer elements.

Figure 8:
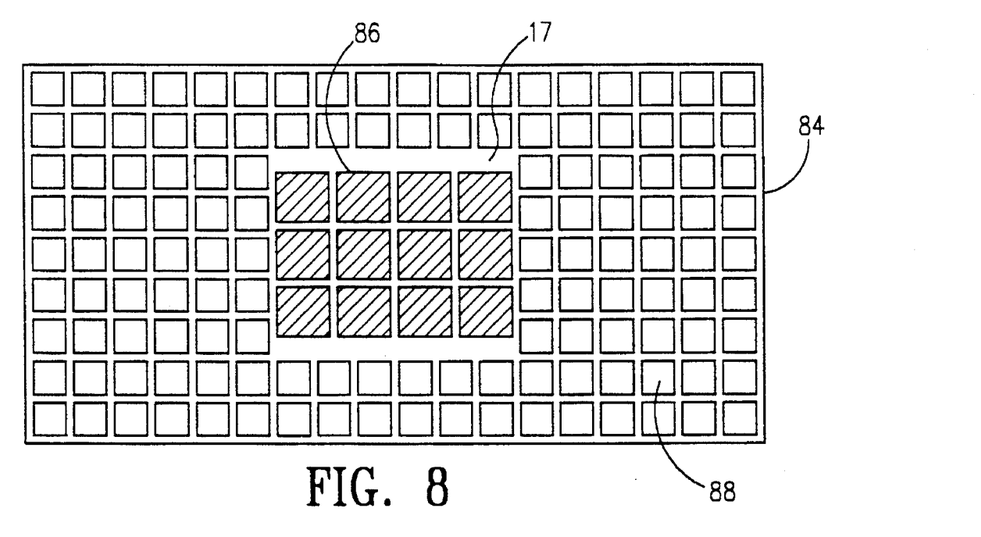
FIG. 8 illustrates a third embodiment of an ultrasonic transducer assembly in accordance with the present invention.

FIG. 8 illustrates a third embodiment of an ultrasonic transducer assembly 84 in accordance with the present invention. In this third embodiment, the plurality of therapeutic transducer elements comprises a multiplexed phased array of therapeutic transducer elements 86, and the plurality of diagnostic transducer elements comprises a multiplexed phased array of diagnostic transducer elements 88. As in the first and second embodiments, the array of therapeutic transducer elements 86 is disposed centrally of the array of diagnostic transducer elements on a common platform. Suitable backing and matching materials are employed in the same manner as in the previous embodiments. This embodiment can be used for treatment of areas close to the surface of a patient's skin.

Figure 9:
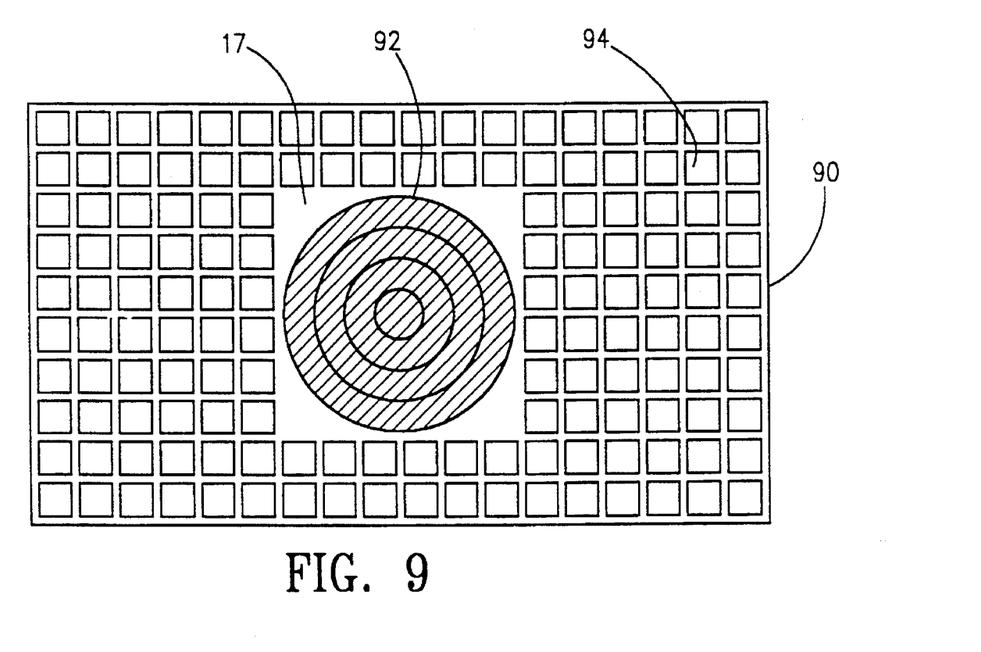
FIG. 9 illustrates a fourth embodiment of an ultrasonic transducer assembly in accordance with the present invention.

FIG. 9 illustrates a fourth embodiment of an ultrasonic transducer assembly 90 in accordance with the present invention. This fourth embodiment differs from the third embodiment in that the plurality of therapeutic transducer elements comprise an annular array of therapeutic transducer elements 92. As in the previous embodiments, the annular array of therapeutic transducer elements 92 is disposed centrally of the array of diagnostic transducer elements 94 on a common platform. Suitable backing and matching materials are employed in the same manner as in the previous embodiments. This embodiment can be used for treatment close to the surface of a patient's skin and for treatment to medium depths.

As those skilled in the art can appreciate, the circuitry of FIGS. 6 and 7 must be modified in a conventional manner to operate with the multiplexed phased transducer arrays of the third and fourth embodiments.

In each of the foregoing embodiments, the therapeutic transducer elements are disposed centrally of the diagnostic transducer elements. Placing the diagnostic transducer elements outwardly from the centrally located therapeutic elements enlarges the field of view of the transducer assembly, increases the imaging sensitivity of the assembly and increases the resolution of images obtained using the transducer assembly.

The ultrasonic transducer assembly of the present invention can be incorporated into specialized ultrasonic probes to enable an operator to bring the transducer assembly closer to anatomical regions of interest. In this manner tissue differentiation can be more easily discerned, and an enhanced resolution and wider field of view can be achieved.

Figure 10A:
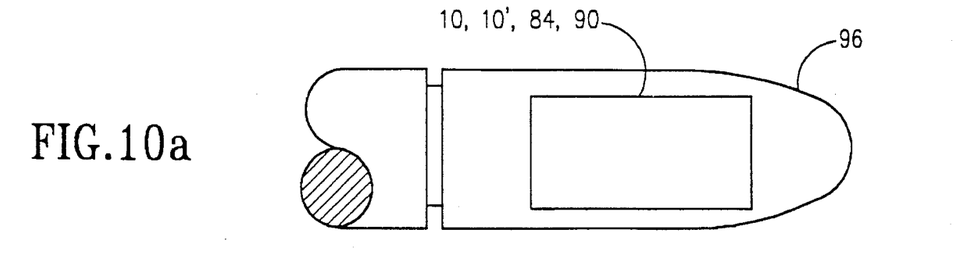
Figure 10B:
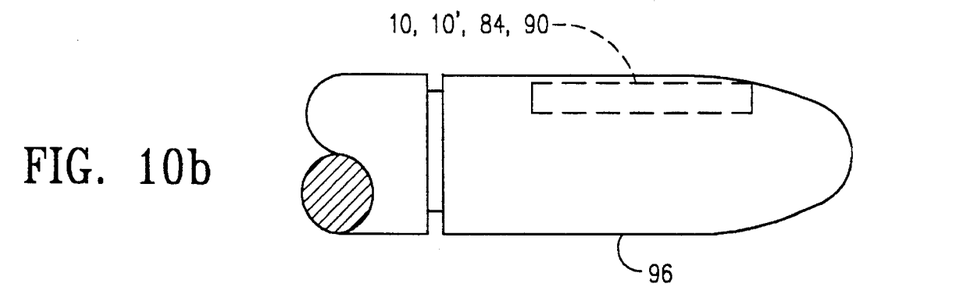

FIGS. 10 (*a*) and (*b*) show different views of a transesophageal probe 96 incorporating a transducer assembly in accordance with any one of the foregoing embodiments 10, 10', 84, 90 of the present invention. The transducer assembly is placed at the tip of the probe. The transesophageal probe can be used for imaging tissues and the heart from within the esophagus. The ultrasonic transducer assembly can be rotated manually through an angle of approximately 180 degrees. The transducer assembly can also be rotated in the anterior and posterior directions at angles of up to 120 degrees. The transducer assembly can still further be moved/rotated to the left and right with an angle of rotation of up to 90 degrees.

Figure 11A:
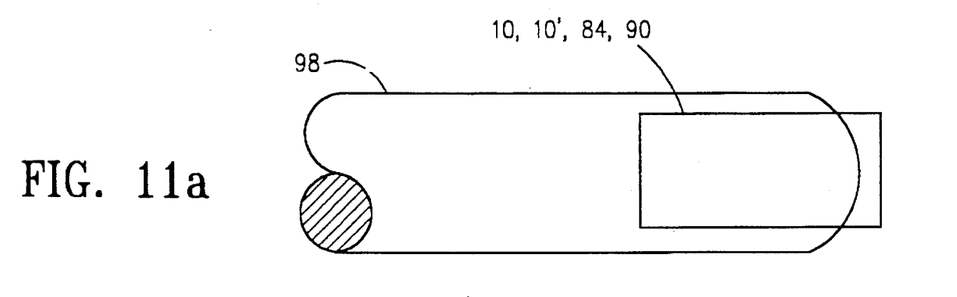
Figure 11B:
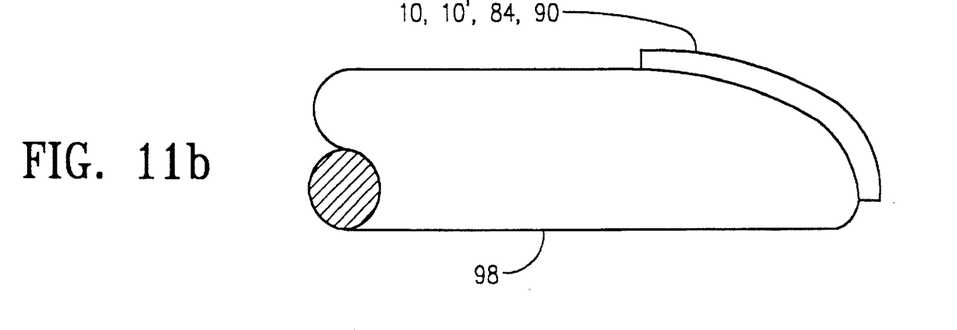

FIGS. 11 (*a*) and (*b*) show different views of one configuration of an intracavitary probe 98 incorporating a transducer assembly in accordance any one of the embodiments 10, 10', 84, 90 described above. The intracavitary probe 98 of FIGS. 11 (*a*) and (*b*) can be used in endovaginal applications. As best shown in FIG. 11, the platform of the transducer assembly can be contoured to suit the particular application.

Figure 12A:
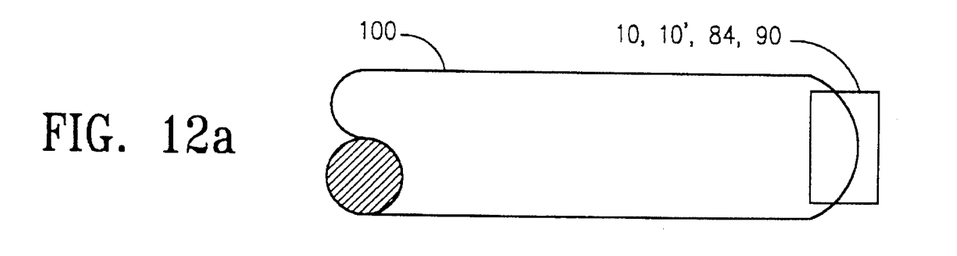
Figure 12B:
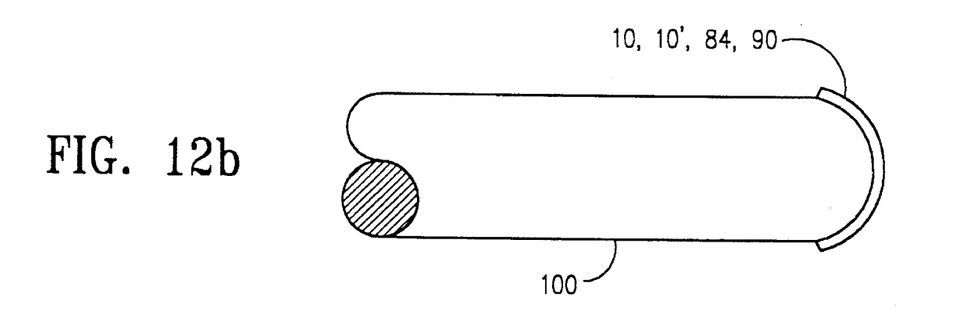

FIGS. 12 (*a*) and (*b*) show different views of a second configuration of an intracavitary probe 100 incorporating a transducer assembly in accordance with any one of the foregoing embodiments. In this configuration, the transducer assembly is located at the extreme tip of the probe 100. Such a configuration can be used in endovaginal applications, or can be used for imaging the prostate.

Figure 13:
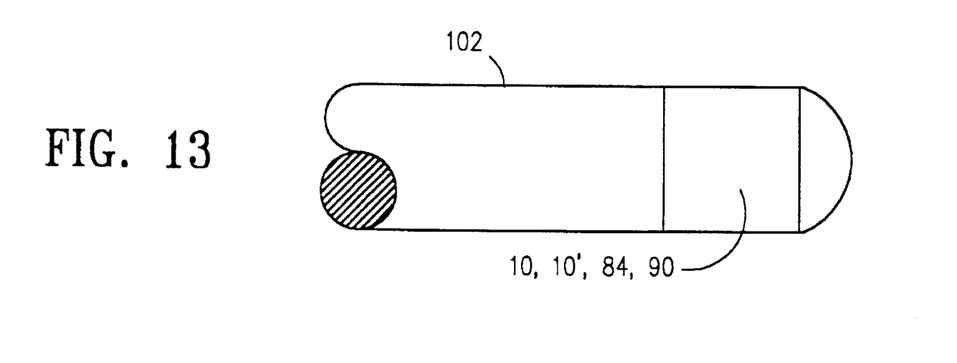
FIG. 13 shows a third configuration of an intracavitary probe incorporating an ultrasonic transducer assembly in accordance with the present invention.

FIG. 13 shows a third configuration of an intracavitary probe 102 incorporating a transducer assembly in accordance with any one of the foregoing embodiments. In this configuration, the transducer assembly encircles the shaft of the probe just below the tip. This configuration can be used for either endovaginal or endorectal imaging.

According to another aspect of the present invention, a novel method is provided wherein ultrasonic imaging of vesicles in a region of a patient is carried out simultaneously with the application of therapeutic ultrasonic waves in order to rupture the vesicles for purposes, such as, for example, enhanced cavitation or the targeted release of a bioactive agent combined with the vesicles. The method comprises the steps of (i) administering to the patient a quantity of vesicles; (ii) insonating the vesicles in a region of the patient with therapeutic ultrasonic waves at a frequency and energy to cause the vesicles to rupture; and (iii) simultaneously receiving ultrasonic emissions from the insonated vesicles at a harmonic of the frequency of the therapeutic ultrasonic waves and generating an image of said region from the received ultrasonic emissions. Simultaneous imaging allows an operator to monitor the rupture of the vesicles in real time.

As one skilled in the art would recognize once armed with the present disclosure, widely varying amounts of vesicles may be employed in the practice of the method of the present invention. As used herein, the term "quantity of vesicles" is intended to encompass all such amounts.

It is known that bubbles suspended in a liquid, such as the administered vesicles described herein, can be made to emit ultrasonic energy when exposed to ultrasonic waves. See, e.g., D. L. Miller, "Ultrasonic Detection of Resonant Cavitation Bubbles in a Flow Tube by their Second Harmonic Emissions," *Ultrasonics*, pp. 217–224 (September 1981), the disclosure of which is hereby incorporated by reference. Emission of ultrasonic energy occurs at harmonics of the incident frequency. The method of the present invention takes advantage of this known property to allow an operator to image the vesicles of a vesicle formulation simultaneously with the application of therapeutic ultrasonic waves for the purpose of rupturing the vesicles. The therapeutic ultrasonic waves serve to produce the harmonic emissions in the vesicles prior to their rupture.

Emission at twice the frequency of the incident ultrasonic waves, called second harmonic emissions, are the strongest harmonic emissions at low amplitudes. Preferably, it is these so-called second harmonic emissions that are received in the aforementioned receiving step. It is desirable where possible to insonate the vesicles at a frequency which is close to optimal for eliciting maximal second harmonic signals, and this will vary depending upon the diameter, elasticity, and density of the vesicles. Of course, imaging can be performed at other harmonic frequencies, including both even and odd harmonic frequencies, if desired. Imaging at harmonics and sub-harmonics of an excitation frequency is described in U.S. Pat. No. 5,410,516, the disclosure of which is hereby incorporated by reference in its entirety.

In order to achieve rupture of the vesicles, continuous wave therapeutic ultrasound is preferred, although the sound energy may be pulsed also. If pulsed sound energy is used, the sound will generally be pulsed in echo train lengths of about 8 to about 20 or more pulses at a time. Preferably, the echo train lengths are about 20 pulses at a time.

Energy levels of the therapeutic ultrasonic waves used to insonate the vesicles are preferably in the range of about 0.05 Watt (W) per square centimeter ($cm^2$) to about 5.0 $W/cm^2$, with energy levels of about 0.2 to about 2.5 $W/cm^2$ being preferred. For very small vesicles, for example, vesicles having a diameter of less than about 0.5 micron, higher frequency ultrasonic waves are generally preferred. This is because smaller vesicles are capable of absorbing ultrasonic energy more effectively at higher frequencies. External application may be preferred for the skin and other superficial tissues, but for deep structures, the application of sonic energy via interstitial probes or intracavitary probes of the type described above may be preferred.

Experiments have shown that the onset of vesicle rupture occurs at the following spatial peak temporal average intensities ($I_{SPTA}$), in milli-Watts (mW) per centimeter squared ($cm^2$), for continuous-wave and selected duty cycles of ultrasonic waves. All values were obtained using a ultrasonic waves having a frequency of 1.0 MHz.

| Duty Cycles | $I_{SPTA}$ (mW/cm$^2$) |
| --- | --- |
| 5.3% | 290 |
| 10.4% | 100 |
| 21.9% | 70 |
| Continuous Wave | 35 |

As these data reveal, rupture occurs most easily with continuous wave ultrasound.

Vesicles can be administered to the patient in a variety of forms adapted to the chosen route of administration, namely, parenterally, orally, or intraperitoneally. Parenteral administration, which is preferred, includes administration by the following routes: intravenous; intramuscular; interstitially; intraarterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration.

The useful dosage to be administered and the mode of administration will vary depending upon the age, weight, and type of animal to be treated, and the particular therapeutic application intended. Typically, dosage is initiated at lower levels and increased until the desired therapeutic effect is achieved.

The patient may be any type of animal, but is preferably a vertebrate, more preferably a mammal, and most preferably human. By region of a patient, it is meant the whole patient, or a particular area or portion of the patient.

The method of the present invention can also be carried out in vitro. For example, in cell culture applications, the vesicles may be added to the cells in cultures and then incubated. Therapeutic ultrasonic waves can then be applied to the culture media containing the cells and vesicles.

The method of the present invention is most advantageously carried out using the novel ultrasonic transducer assemblies of the present invention. For example, considering the ultrasonic transducer assembly 10 of FIG. 1, the linear array of therapeutic transducer elements 16 can be used to perform the insonating step at a first frequency, such as 1.75 MHz, while the first and second linear arrays of diagnostic transducer elements 12, 14 can be fabricated and employed to receive the harmonic emissions of the vesicles at twice the incident frequency, i.e., 3.5 MHz.

EXAMPLES

The method of the present invention is further described in the following prophetic examples. These prophetic examples are for illustrative purposes only, and are not to be construed as limiting the appended claims.

Example 1

In a patient with a malignant soft tissue sarcoma of the thigh, 5.0 cubic centimeters (cc) of a vesicle formulation, $1.5 \times 10^9$ vesicles/milliliter (ml), combining 5 milligrams (mg) of doxorubicin is injected intravenously (IV). The patient's tumor is ultrasonically imaged via a plurality of diagnostic transducer elements. As the vesicles pass through the tumor's microvasculature, they are detected via gray scale imaging and color Doppler. Upon detection, therapeutic ultrasonic waves are applied in bursts of 10 seconds using continuous wave ultrasound at a frequency of 1.5 MHz and energy of 0.5 W/cm$^2$. The diagnostic transducer elements are employed to receive second harmonic emissions from the vesicles at a frequency of 3.0 MHz, twice the incident frequency of the therapeutic ultrasonic waves. As the vesicles rupture, the doxorubicin is released locally within the tumor. Simultaneous imaging in accordance with the methods and apparatus of the present invention allows the physician to monitor the rupture of vesicles in real-time. High intra-tumoral concentrations of chemotherapy are attained, and the patient's tumor is eradicated.

Example 2

In a patient with breast cancer, 5.0 cc of a vesicle formulation comprising perfluoropentane vesicles labeled with antibodies to breast cancer epitopes is injected IV. Approximately 48 hours later, ultrasonic imaging of the patient's axilla is performed. A plurality of therapeutic transducer elements are employed to generate incident ultrasonic waves at a frequency insufficient to cause vesicle rupture, but sufficient to produce second harmonic emissions. Once second harmonic emissions are received from lymph nodes binding the antibody bearing vesicles, the energy of the therapeutic ultrasonic waves is increased to 5.0 W/cm$^2$. The tumor bonded with vesicles lowers the cavitation threshold and local intra nodal cavitation is achieved destroying the malignant tumor. Simultaneous imaging of the destruction is achieved via the plurality of diagnostic transducer elements.

Example 3

The same as example 2, except that the vesicles also contain 1.0 mg per ml of cis-platinum. A lower energy of 0.5 W/cm$^2$ is applied to rupture the vesicles and release the cis-platinum within the lymph nodes, destroying the tumor.

Example 4

In a patient with myocardial ischemia involving the left anterior wall, 2.0 cc of cationic vesicles ($1.0 \times 10^9$ vesicles/ml) binding the gene for endothelial growth factor (EFG) is injected IV. Continuous wave therapeutic ultrasound is applied in bursts at energies of between 0.05 and 0.2 W/cm$^2$ to the left ventricular anterior wall myocardium. As the vesicles pass through the microvasculature of the anterior wall myocardial tissue, the vesicles are ruptured. Rupture of the vesicles not only releases the genes into the myocardium but also creates local shock waves which facilitate passage of the genetic material into the cardiac endothelial and myocyte cells. Local gene expression into EFG is achieved with resultant growth of new coronary circulation and improvement in coronary blood flow. Rupture of the vesicles is monitored in real time via the second harmonic emissions received by a plurality of diagnostic transducer elements.

Example 5

A patient with locally invasive esophageal cancer is treated with bubbles bearing mitomycin-C and the gene for BCL-2. An endoesophageal transducer, such as the probe illustrated in FIGS. 10(a) and (b), is placed in the esophagus and the position of the transducer is confirmed via the plurality of diagnostic transducer elements. A 10.0 ml vesicle formulation binding drug and genetic material is then injected IV. As the vesicles pass through the tumor they are ruptured using bursts of 0.5 W/cm$^2$ therapeutic ultrasonic waves. Rupture of the vesicles is monitored in real time. The therapy results in elimination of the tumor.

Example 6

As in example 5, except that the patient has pancreatic cancer. The transducer assembly is placed into the stomach and positioned such that imaging is performed through the posterior wall of the stomach. The pancreatic tumor is localized, the vesicle formulation is injected as in example 5, and therapy is performed while simultaneously imaging the rupture of the vesicles. The patient achieves a remission of pancreatic carcinoma.

Example 7

A patient with atherosclerosis is administered a 5.0 cc vesicle formulation having vesicles less than 1.0 micrometer (μm) in diameter, which are labeled with cholesterol. The vesicles accumulate in regions of lipid laden plaque. Transcutaneous therapeutic ultrasonic waves are then applied with an energy of 0.5 W/cm$^2$. The vesicles rupture as they lyse the plaque. Rupture of the vesicles is monitored in real-time.

Example 8

As in example 7, except that the vesicles are targeted to the atherosclerotic plaque by labeling with low density lipoproteins (LPL).

Example 9

As in example 7, except that the antisense construct to basic fibroblastic growth factor is applied to eliminate intimal hyperplasia and restenosis.

Example 10

As in examples 7 and 8, except that an endovascular catheter equipped with an ultrasonic transducer assembly is employed. The vesicles within the arterial plaque are then burst from within the vessel using the therapeutic transducer elements on the endovascular catheter.

Example 11

In a patient with prostate cancer, 10 ml of a vesicle formulation binding 10 mg of anti LHRH decapeptide are injected IV. An endorectal probe with an ultrasonic transducer assembly of the present invention is placed within the rectum and positioned adjacent the prostate gland with the aid of the diagnostic transducer elements. As the vesicles are detected coursing within the microvasculature of the prostatic tumor, high energy therapeutic ultrasonic waves are applied, and the vesicles are ruptured, releasing high local concentrations of the inhibitory peptide. Simultaneous imaging of the vesicles is performed via second harmonic emissions. Tumor regression is thus achieved from an outpatient, minimally invasive procedure.

The disclosures of each patent, patent application and publication cited or described in this document are hereby incorporated by reference, in their entirety.

As the foregoing illustrates, the present invention is directed to novel methods and apparatus for performing diagnostic ultrasound simultaneously with the application of therapeutic ultrasonic waves to a region of a patient. In particular, the methods and apparatus of the present invention are advantageous in performing ultrasonic imaging of a region of a patient while simultaneously applying therapeutic ultrasonic waves to the region in order to rupture vesicles in the region for therapeutic purposes, such as, for example, the targeted release of a bioactive agent. The methods and apparatus of the present invention allow an operator to monitor the rupture of vesicles in real time. It is understood that changes may be made to the embodiments described above without departing from the broad inventive concepts thereof. Accordingly, the present invention is not limited to the particular embodiments disclosed, but is intended to cover all modifications that are within the spirit and scope of the invention as defined by the appended claims.

What is claimed is:

1. An ultrasonic transducer assembly for simultaneous application of diagnostic and therapeutic ultrasonic waves comprising:

a plurality of therapeutic transducer elements for generating therapeutic ultrasonic waves;

a plurality of diagnostic transducer elements for generating and receiving diagnostic ultrasonic waves; and a platform having a substantially planar upper surface on which said pluralities of therapeutic and diagnostic transducer elements are arranged, said plurality of therapeutic transducer elements being disposed on said planar surface centrally of said plurality of diagnostic transducer elements.

2. The ultrasonic transducer assembly of claim 1 further comprising a first backing material disposed between said plurality of therapeutic transducer elements and the planar surface of said platform, and a second backing material disposed between said plurality of diagnostic transducer elements and the planar surface of said platform.

3. The ultrasonic transducer assembly of claim 2 wherein said first backing material has a lower acoustic impedance than said second backing material.

4. The ultrasonic transducer assembly of claim 2 wherein said first backing material has an acoustic impedance in the range of about $2 \times 10^6$ Kg/m$^2$/s to $3 \times 10^6$ Kg/m$^2$/s.

5. The ultrasonic transducer assembly of claim 2 wherein said second backing material has an acoustic impedance of about $7 \times 10^6$ Kg/m$^2$/s.

6. The ultrasonic transducer assembly of claim 2 wherein said first and second backing materials are each formed of a polymer matrix material.

7. The ultrasonic transducer assembly of claim 2 wherein said first backing material comprises one of an epoxy with tungsten powder and air.

8. The ultrasonic transducer assembly of claim 2 wherein said second backing material comprises an epoxy with tungsten powder.

9. The ultrasonic transducer assembly of claim 1 wherein said plurality of therapeutic transducer elements are isolated from said plurality of diagnostic transducer elements on said planar surface by a material having a heavily damped acoustic impedance.

10. The ultrasonic transducer assembly of claim 9 wherein said acoustic insulating material comprises one of neoprene and air.

11. The ultrasonic transducer assembly of claim 1 wherein said plurality of therapeutic transducer elements comprises a linear array of therapeutic transducer elements, and wherein said plurality of diagnostic transducer elements comprises first and second linear arrays of diagnostic transducer elements disposed on opposite sides of said linear array of therapeutic transducer elements.

12. The ultrasonic transducer assembly of claim 1 wherein said plurality of therapeutic transducer elements comprises a multiplexed phased array of therapeutic transducer elements, and said plurality of diagnostic transducer elements comprises a multiplexed phased array of diagnostic transducer elements that surround the multiplexed phased array of therapeutic transducer elements on said planar surface.

13. The ultrasonic transducer assembly of claim 1 wherein said plurality of therapeutic transducer elements comprises an annular array of therapeutic transducer elements, and said plurality of diagnostic transducer elements comprises a multiplexed phased array of diagnostic transducer elements that surround the annular array of therapeutic transducer elements on said planar surface.

14. The ultrasonic transducer assembly of claim 1 further comprising a layer of an impedance matching material disposed in facing relation over said therapeutic and diagnostic transducer elements on a side opposite said platform.

15. A method for treating a patient comprising the steps of:

(i) administering to the patient a quantity of vesicles;

(ii) insonating the vesicles in a region of the patient with therapeutic ultrasonic waves at a frequency and energy to cause the vesicles to rupture; and (iii) simultaneously receiving ultrasonic emissions from the insonated vesicles at a harmonic of the frequency of the therapeutic ultrasonic waves and generating an image of said region from the received ultrasonic emissions.

16. The method recited in claim 15 wherein the therapeutic ultrasonic waves comprise continuous-wave ultrasonic signals.

17. The method recited in claim 15 wherein the therapeutic ultrasonic waves are pulsed.

18. The method recited in claim 15 wherein the harmonic at which the ultrasonic emissions of said vesicles are received comprises a second harmonic of the frequency of said therapeutic ultrasonic waves.

19. The method recited in claim 15 wherein said image is generated in real-time.

20. The method recited in claim 15 further comprising the step of monitoring the vesicles using diagnostic ultrasonic waves to determined the presence of the vesicles in said region prior to said insonating step.

21. The method recited in claim 15 wherein the vesicles are administered intravenously.

22. The method recited in claim 15 wherein the vesicles are combined with a bioactive agent to form a vesicle formulation, rupture of the vesicles causing release of the bioactive agent into the region.

23. The method recited in claim 15 wherein said insonating step is performed using a plurality of therapeutic transducer elements, and said receiving step is performed simultaneously using a plurality of diagnostic transducer elements, wherein the plurality of therapeutic transducer elements are located centrally of the plurality of diagnostic transducer elements on a common platform.

24. The method recited in claim 15 wherein the frequency of the therapeutic ultrasonic waves is in the range of about 0.75 to about 3.0 MHz.

25. The method recited in claim 24 wherein the frequency of the therapeutic ultrasonic waves is in the range of about 1.0 to about 2.0 MHz.

26. The method recited in claim 15 wherein the energy of said therapeutic ultrasonic waves is in the range of about 0.05 W/cm$^2$ to about 5.0 W/cm$^2$.

27. The method recited in claim 26 wherein the energy of said therapeutic ultrasonic waves is in the range of about 0.2 W/cm$^2$ to about 2.5 W/cm$^2$.

* * * * *

UNITED STATES PATENT AND TRADEMARK OFFICE
CERTIFICATE OF CORRECTION

PATENT NO. : 5,558,092
DATED : Sep. 24, 1996
INVENTOR(S) : Unger et al.

It is certified that error appears in the above-indentified patent and that said Letters Patent is hereby corrected as shown below:

On title page, at [56], under OTHER PUBLICATIONS, at Fessenden, P. et al., after "*Engineering*", please delete "1994," and insert --1984,-- therefor.

On page 2, under OTHER PUBLICATIONS, at Hinders, M.K. et al., please delete "Ultrasound-hperthermia" and insert --Ultrasound-hyperthermia-- therefor.

In column 18, claim 20, line 64, please delete "determined" and insert --determine-- therefor.

Signed and Sealed this

Thirty-first Day of December, 1996

Attest:

BRUCE LEHMAN

*Attesting Officer*   *Commissioner of Patents and Trademarks*